Figure 1:
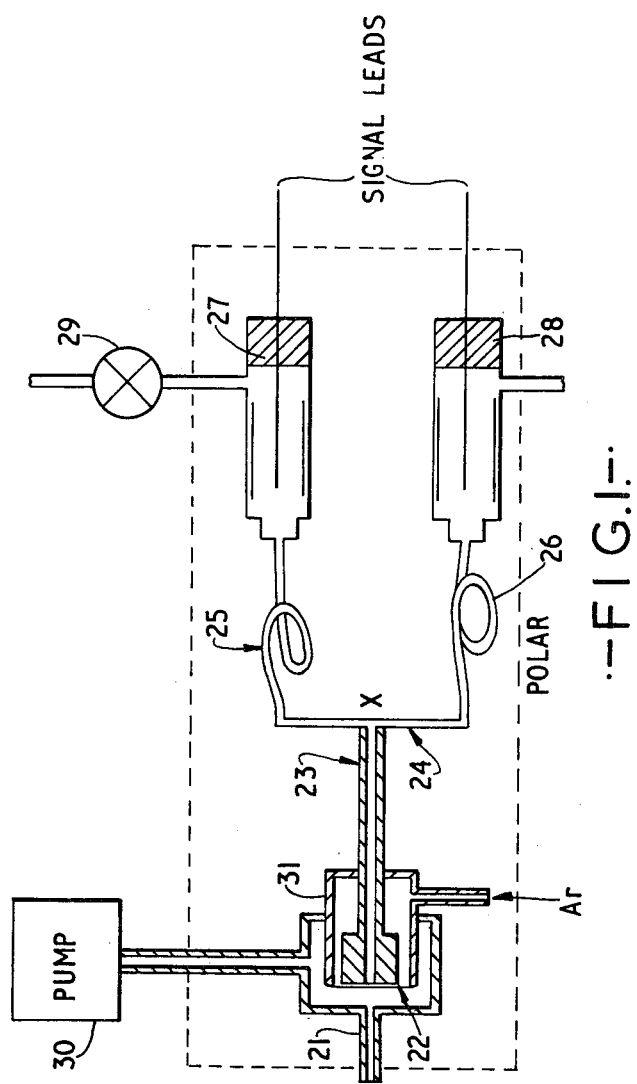

United States Patent [19]

Jenkins et al.

[11] 4,116,042
[45] Sep. 26, 1978

[54] METHOD AND APPARATUS FOR DETECTING A CONSTITUENT IN AN ATMOSPHERE

[76] Inventors: Anthony Jenkins, 54 Finchams Close, Linton, Cambridgeshire; Douglas Walter Isgrove, 144 Malvern Rd., Cherryhinton, Cambridgeshire, both of England

[21] Appl. No.: 742,907
[22] Filed: Nov. 18, 1976
[30] Foreign Application Priority Data
Nov. 20, 1975 [GB] United Kingdom ............... 47727/75
[51] Int. Cl.² ....................... G01N 31/06; G01N 33/22
[52] U.S. Cl. ........................................................ 73/23
[58] Field of Search ................... 73/23, 23.1, 421.5 R; 23/232 R, 232 C, 254 R

[56] References Cited
U.S. PATENT DOCUMENTS

| | | |
|---|---|---|
| 3,263,488 | 8/1966 | Martin .................................. 73/23.1 |
| 3,386,279 | 6/1968 | Sternberg .............................. 73/23.1 |
| 3,430,482 | 3/1969 | Draynieks et al. .................. 73/23.1 |
| 3,443,415 | 5/1969 | Clardy .................................. 73/23.1 |
| 3,942,357 | 3/1976 | Jenkins ..................................... 73/23 |
| 3,997,297 | 12/1976 | Jenkins et al. ........................... 73/23 |

*Primary Examiner*—Stephen A. Kreitman
*Attorney, Agent, or Firm*—Anthony J. Casella

[57] ABSTRACT

A method and apparatus for detecting the presence of a particular constituent in a sampled atmosphere. The sampled atmosphere is drawn along two substantially identical flow paths, each path containing a detector. The flow of the particular constituent is delayed along one path only but not the other path to separate, in time, the signals from the two detectors. Means are provided for obtaining a resultant difference signal and for utilizing the difference signal to provide a positive identification of the presence of the particular constituent in the sampled atmosphere.

5 Claims, 8 Drawing Figures

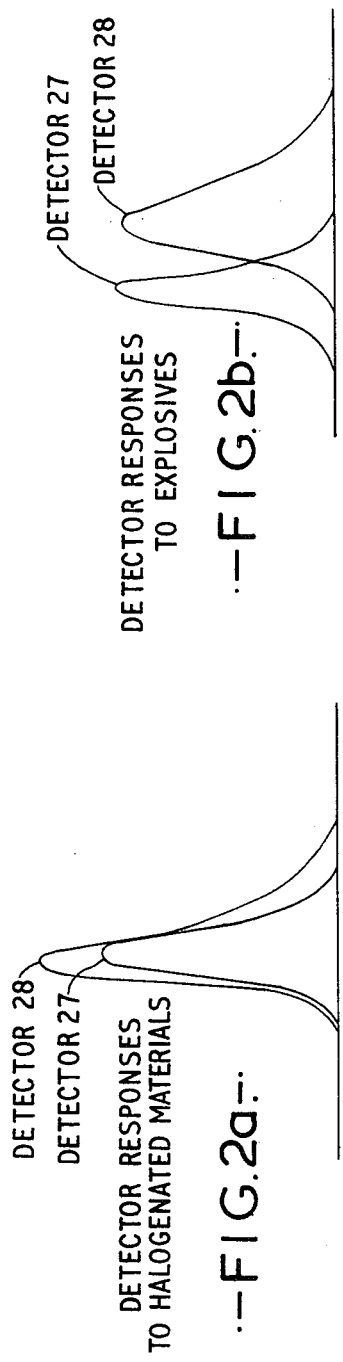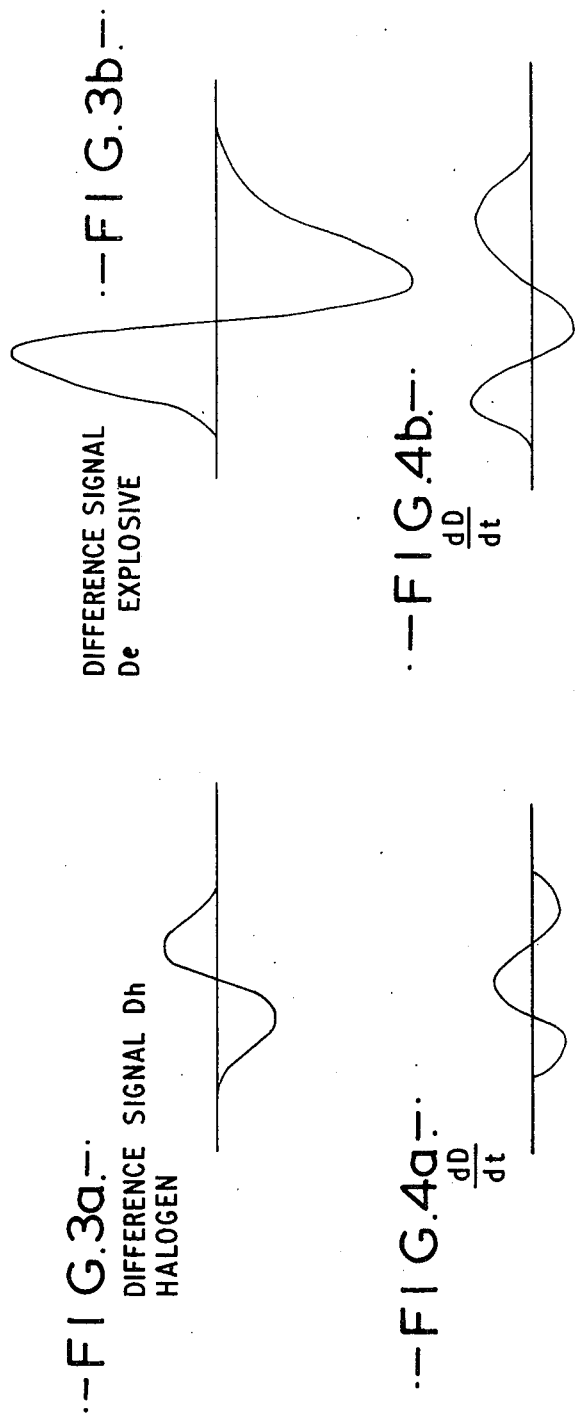

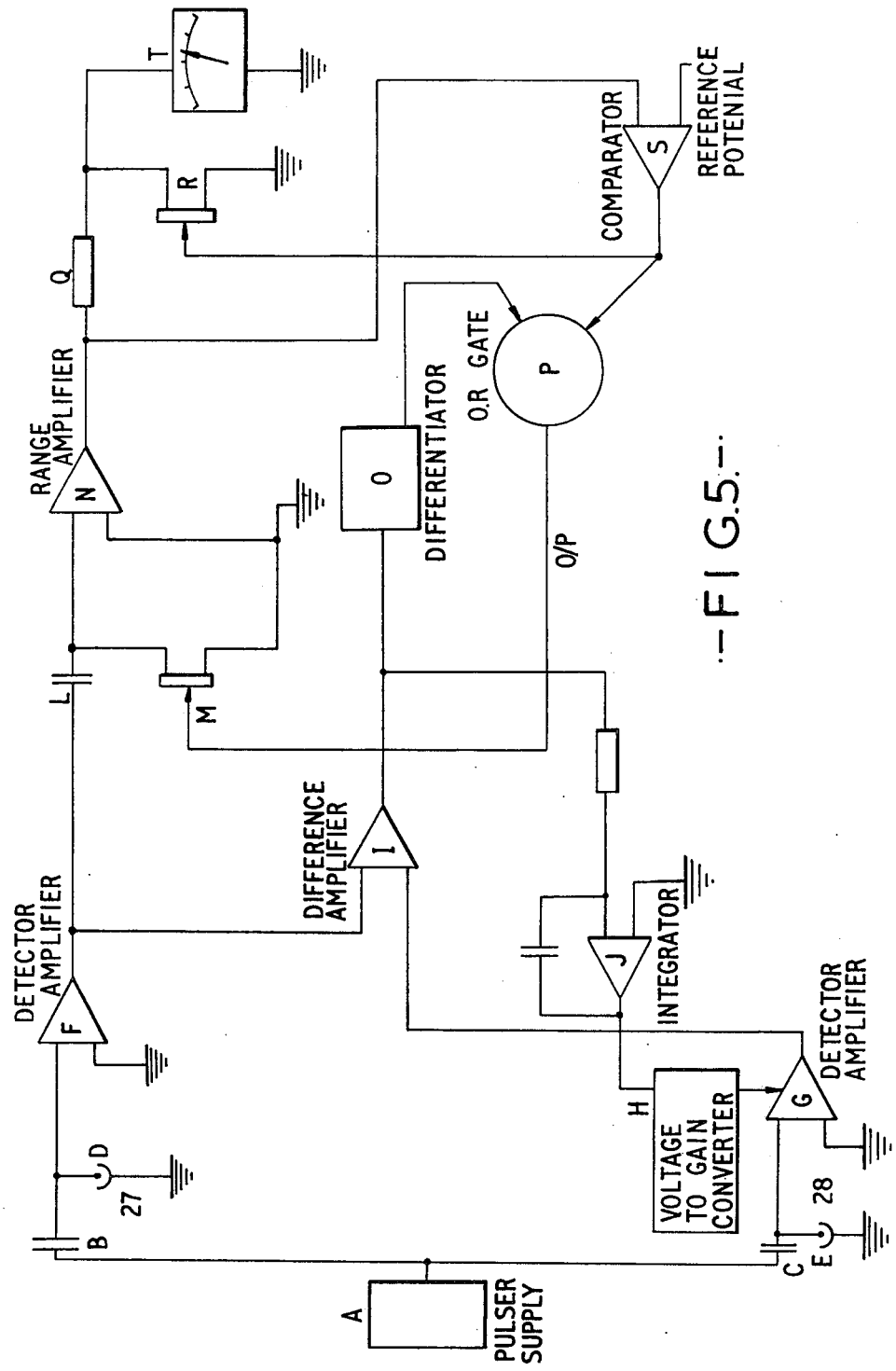
-FIG.5.-

METHOD AND APPARATUS FOR DETECTING A CONSTITUENT IN AN ATMOSPHERE

The present invention concerns a method and apparatus for detecting the presence of a particular constituent in an atmosphere.

In order to positively detect a particular constituent in an atmosphere it is required to ensure that any detector system will respond to the presence of the constituent and will not be sensitive to the presence of other constituents which might produce signals which could mask the required signal. Where a detector system is responsive to more than one possible atmospheric constituent difficulty can arise in relating any resulting signal to a particular constituent.

The particular constituent of interest can be the vapours emitted from nitro-compounds present in explosives. Such vapours can be detected by an electron capture detector but in general the atmosphere being sampled will also contain other constituents, such as halogenated hydrocarbons, which also produce responses in electron capture detectors.

An existing method and apparatus for detecting the presence of a particular constituent in an atmosphere comprises drawing a sample of the atmosphere along two substantially identical flow paths, each path containing a detector capable of detecting the particular constituent, and converting the particular constituent content in one but not the other of the flow paths into matter incapable of producing a response in the associated detector such that in the absence of the particular constituent in the atmosphere no significant difference is detectable between the signals emitted by the two detectors as the flows along the two paths are substantially identical but in the presence of the particular constituent the flow content along said one path is altered to change the signal from the associated detector and the resultant difference in signals is indicative of the presence of the particular constituent in the atmosphere.

For the detection of explosives the arrangement mentioned above converts the explosives vapours flowing along said one path into matter incapable of producing a response in the associated detector by thermal degradation. However some explosives vapours do not readily break down with heat and further the power required to ensure that the temperature of said one path reaches a value sufficient to ensure the break down of all the explosive vapours flowing therealong can be appreciable. This can be a disadvantage, particularly for a portable apparatus required to operate off a battery supply.

Accordingly, the present invention provides an alternative method and apparatus for determining the presence in an atmosphere of a particular constituent.

According to one aspect of the present invention a method of detecting the presence of a particular constituent in an atmosphere comprises drawing a sample of the atmosphere along two flow paths, each path containing a detector, changing the flow time of the particular constituent of interest along one of the paths only but not theother of the paths to separate the signals from the two detectors obtaining a resultant difference in the signals from the two detectors and utilising the difference signal to indicate the presence of the particular constituent of interest in the atmosphere.

According to another aspect of the present invention an apparatus for detecting the presence of a particular constituent in an atmosphere comprises first and second substantially flow path for receiving sample atmosphere, each path containing a detector, means included in one path only for altering the flow time of the particular constituent along said one path to the associated detector whereby to separate the signals from the detectors and means for obtaining a resultant difference in signals from the two detectors, said resultant difference signal being utilised to indicate the presence of the particular constituent in the atmosphere.

The invention will be described further, by way of example, with reference to the accompanying drawings; in which:

FIG. 1 is a diagrammatic arrangement of an apparatus according to the invention;

FIGS. 2 to 4 inclusive are schematic signal diagrame;

FIG. 5 is a circuit diagram of the apparatus.

In FIG. 1, an atmosphere, such as air, to be sampled is drawn through a probe or nozzle 21 by means of a pump 30 to impinge on a membrane 22 secured across the open end of a chamber 31. The membrane, for example a silastomer such as a methyl silicone elastomer membrane, is such as to allow organic vapours, for example vapours from nitro-explosives and halocompounds to pass therethrough while forming a barrier to oxygen and other constituents of the atmosphere. Such a barrier is desirable as oxygen is itself an electron absorber and capable of producing a response in an electron capture detector. The rear of the membrane is swept by a flow of an inert carrier gas, conveniently Argon. Vapours passing through the membrane are conveyed by the carrier gas along a conduit 23 and divide at junction X into two substantially identical flow paths 25 and 26. The two paths 25 and 26 terminate in respective electron capture detectors 27 and 28. The two detectors 27 and 28 are chosen to be as similar as possible. The flow exhausts to the atmosphere from the two detectors and a flow control member 29, such as a needle valve, is included in the exhaust path from the detector 27. Alternatively, the control member can be arranged in the path 25. The apparatus within the region bounded by the rectangular dotted outline is preferably maintained at a temperature at which the possibility of vapours of interest sticking to the walls of the flow paths is reduced to a minimum. A temperature within the range 75° C. to 150° C. is suitable for this purpose.

The paths 25 and 26 can comprise chromatographic columns, which conveniently are coiled to provide a compact apparatus. The columns can contain an inert packing material with the material in column 26 coated with a polar liquid phase. Alternatively, the columns can both be open with a polar coating applied to the wall of column 26. As a result polar material, that is in the present case the vapours from explosives, will be delayed in the column 26 whereas the non-polar material such as halogenated hydrocarbons will pass along both columns 25 and 26 at the speed of the carrier gas. A suitable polar coating for use with explosives vapours is polyethylene glycol.

In brief, an electron capture detector can comprise an ionisation cell having a pair of spaced apart electrodes and containing a source of ionising radiation such as tritium or $Ni_{63}$. A carrier gas on flowing through the detector is ionised by emission from the source. By applying a voltage between the electrodes, and conveniently the voltage is pulsed, the free electrons formed by the ionising emission are collected at the anode to provide a detector standing current. If a trace of material containing molecules which are electron absorbing (the electron capture material) is introduced into the carrier gas flowing through the detector some of the free electrons will be electron capture material) is introduced into the carrier gas flowing through the detector some of the free electrons will be captured by these molecules. The result is detectable by a change in the standing current.

When the atmosphere is being sampled for the presence of say vapours from explosives it is always possible, and indeed probable, that traces of other electron capture materials are present in the atmosphere. For example, the sampled atmosphere can well contain halogenated hydrocarbons which are to be found in pesticides and the like. To avoid any confusion, the apparatus ensures that in the absence of explosives vapours the signal from the detector 27 is behind the signal from the detector 28 but in the presence of explosives the signal from the detector 27 is in advance of the signal from the detector 28.

The gas flow along path 25 can be adjusted by means of the control member 29 to be less than the flow along the path 26. As a result the non-polar volatile material, e.g. halogenated material, entering both paths at junction X will pass along path 26 and into the detector 28 slightly in advance of the corresponding flow along the path 25 into the detector 27. FIG. 2a depicts examples of responses obtained from the two detectors 27 an 28 to halogenated material in the two flow paths. The response from detector 28 is slightly in advance of the response from detector 27.

FIG. 2b shows the responses obtained from the detectors 27 and 28 when the flow along the two paths contains vapour from a nitro-explosive. In this case the flow down path 26 is retarded by the polar material in the column. Consequently the response from detector 27 is in advance of the response from detector 28.

A difference signal from the two signals shown in FIGS. 2a and 2b is shown in FIGS. 3a and 3b respectively. Such a difference signal is used as a basis for distinguishing between, the signals from halogenated material and explosives vapours. As shown in FIG. 2b explosives vapours are characterised by response from detector 27 being in advance of that from detector 28. The response signal from detector 27 is presented to a meter or indicating device only when the response is recognised as resulting from an explosives vapour by means of a circuit shown in FIG. 5.

In order to positively identify the presence of an explosive it is required to provide a circuit which will present a signal from the detector 27 to a meter only for the presence of explosives but which will not pass any other signals arising in the detector 27, for example the signals resulting from the presence of halo-compounds or other electron absorbers in the sampled atmosphere. As seen from FIG. 2a an explosives is characterised by the appearance of the signal in the detector 27 before that in the detector 28. The resulting difference signal has an initial positive portion as seen from FIG. 3b which can be used to unclamp a zeroing circuit which normally prevents the signal from the detector 27 being presented to the meter.

In the case of halogenated material or other non-explosive vapours a positive difference signal can occur over the tailing portion of the signal from the detector 27. This positive difference signal can also unclamp the zeroing circuit leading to undesirable signals appearing at the meter. This difficulty can be overcome by including in the zeroing circuit additional means which isolate the meter when the difference signal arises when the signal at detector 27 is falling towards zero, that is when the slope of the signal at detector 27 is negative.

In practice difficulty can arise in maintaining equal background signals from the two detectors so that an accurate zero difference signal is obtained in the absence of detectable constituents in the sample flow. Accordingly it is preferable to rely upon the differential of the difference signal. The differentials are depicted in FIGS. 4a and 4b for halogenated materials and nitro-explosives respectively.

In FIG. 5, detectors D and E correspond to detectors 27 and 28 respectively. The two detectors are supplied by a common pulsed polarising supply A through two isolating capacitors B and C. The signals from the two detectors are amplified in amplifiers F and G respectively. The gain of amplifier G is adjusted by an automatic voltage to gain converter H in order that the amplified standing currents from the two detectors are substantially equal. The voltage to gain converter H is controlled by the output of a difference amplifier I through an integrating circuit J whose time constant is long compared with normal response times. As a result the gain of amplifier G is only slowly adjusted until the output of the difference amplifier I approaches zero, that is until the standing currents from the detectors are equal.

The signal from amplifier F is fed through a capacitor L to an amplifier N and through a load resistor Q to a meter T. A switching device M, for example a field effect transistor, is connected intermediate the capacitor L and the amplifier N. The opposite side of the switching device M is earthed. The switch M is normally closed to prevent any signal reaching the amplifier N. A second switching device R, again for example a field effect transistor, is connected at one side between the resistor Q and the meter T and the opposite side is at earth potential. Switching device R is normally closed.

Normally closed switching device M is open when "OR" gate P receives a positive signal from differentiator O or a signal appearing at the output of amplifier N. In practice, as the switching device M is normally closed a signal cannot appear at the output of amplifier N and consequently the switching device M can only be opened by a positive signal from the differentiator O. The differentiator O is connected to the difference amplifier I and provides a positive signal to open the switching device M only when an increasing difference signal is obtained between the signals from the two detectors. When the switching device M is opened any change in signal from the detector D is allowed through the amplifier N and the resistor Q. Such a signal cannot however pass to the meter T until the switching device R is opened.

The switching device R is controlled by a comparator S and the comparator functions to open the switching device R when the signal appearing at the output of amplifier N is increasing and exceeds the reference voltage of the comparator. Conveniently this reference voltage can be 10% of full scale of the matter T. As a result only positive signals greater than 10% of the full signal of the meter are presented to the meter. The switching device M is held open by the output from the comparator while the signal at the output from the amplifier N exceeds the reference voltage of the comparator. As a result all of the response signal is presented to the meter T, even though the output of the differentiator may be negative for part of the response.

FIGS. 3a and 3b respectively depict the difference signals resulting from halogens and explosives while FIGS. 4a and 4b depict the differential of the respective difference signals. As seen from FIG. 4a a positive differential of the halogen difference signals occurs when the signal from the detector 27 is tailing or falling. Consequently, the switching device M can open when a difference signal arising from the halogen responses in the two detectors is presented to the differentiator. However the resulting tailing halogen signal from the detector 27 appearing at the output of the amplifier N cannot proceed to the meter T as switching device R remains closed. The switching device R will only open when an increasing signal having a value exceeding a predetermined value appears at the output of the amplifier N. Such a condition arises in the presence of nitro-explosives.

Whilst the above is particularly concerned with the detection of explosives by "sniffing" the atmosphere for vapours emitted by explosives, it will be appreciated that the invention is not confined to such use. Certain drugs emit characteristic vapours and the invention can also be used in the detection of such drugs. Whilst the electron capture detector is particularly sensitive to the presence of nitro-compounds such as originating from explosives, in other applications it might be desirable to employ alternative forms of detector, for example a flame ionisation detector.

We claim:

1. A method of detecting the presence of a particular constituent in an atmosphere which comprises drawing a sample of the atmosphere along two substantially identical flow paths, each path containing a respective detector capable of detecting said particular constituent, delaying the elution time of the particular constituent along one but not the other of the paths and passing the flows to the respective detectors, obtaining a resulting difference in signals from the two detectors, recognizing the presence of said particular constituent in the atmosphere when said difference signal has a positive increasing initial portion and utilizing said positive increasing difference signal to actuate means normally isolating the detector associated with said other flow path from an indicating means whereby to present a signal at said indicating means indicative of the presence of the particular constituent in the atmosphere.

2. An apparatus for detecting the presence of a particular constituent in an atmosphere comprising first and second substantially identical flow paths for receiving sampled atmosphere, each path containing a detector, means included in one path only for altering the elution time of the particular constituent along said one path to the associated detector, indicator means to receive a signal from one of said detectors, isolating means in the signal path from said one detector to the indicator means to prevent the passage of a signal in the absence of said particular constituent in the atmosphere, means for obtaining a resulting difference in signals from the two detectors and means operable in response to a positive increasing difference signal to actuate said isolating means to thereby present a signal at the indicator means which is indicative of the presence of the particular constituent in the atmosphere.

3. An apparatus according to claim 2 in which the means included in one path only is a delay means in said one path and comprises a chromatographic column.

4. An apparatus according to claim 3 in which the column contains an inert packing material coated with a polar liquid phase.

5. An apparatus according to claim 3 in which the column is an open tube with a polar coating applied to the wall thereof.

* * * * *